Figure 1A:
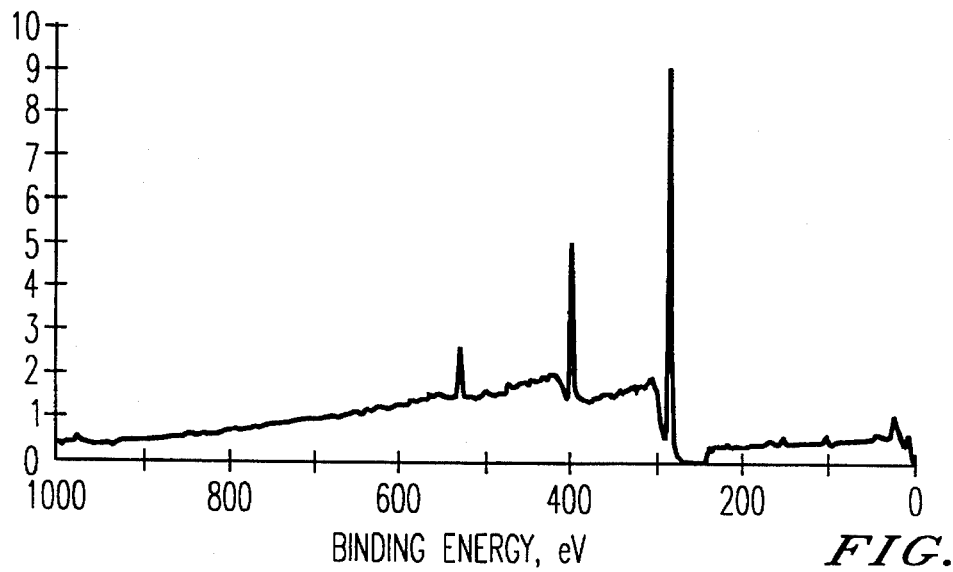

United States Patent [19]

Battistel et al.

[11] Patent Number: 5,599,698
[45] Date of Patent: Feb. 4, 1997

[54] MODIFIED MATERIALS BASED ON POLYACRYLONITRILE AND PROCESS FOR THEIR PRODUCTION

[75] Inventors: Ezio Battistel; Franco Francalanci, both of Novara; Massimo Marinetti, Mestre; Marco Morra, Cortiglione d'Asti, all of Italy

[73] Assignee: Montefibre S.p.A., Milan, Italy

[21] Appl. No.: 448,029

[22] Filed: May 23, 1995

Related U.S. Application Data

[62] Division of Ser. No. 363,875, Dec. 27, 1994.

[51] Int. Cl.$^6$ .............. C12P 13/02; C12N 9/88
[52] U.S. Cl. ............. 435/129; 435/227; 435/232; 435/840
[58] Field of Search ................. 435/129, 232, 435/227, 840

[56] References Cited

U.S. PATENT DOCUMENTS

| | | | |
|---|---|---|---|
| 4,390,631 | 6/1983 | Watanabe et al. | 435/129 |
| 4,851,342 | 7/1989 | Watanabe et al. | 435/129 |
| 4,908,313 | 3/1990 | Satoh et al. | 435/129 |
| 5,302,528 | 4/1994 | Battistel et al. | 435/280 |

Primary Examiner—Herbert J. Lilling
Attorney, Agent, or Firm—Oblon, Spivak, McClelland, Maier & Neustadt, P.C.

[57] ABSTRACT

The invention relates to modified materials based on polyacrylonitrile having amidic groups on their surface. The modification gives the material greater hydrophilic characteristics improving its comfort properties. In addition, it permits the polyacrylonitrile to be dyed also with acidic dyes thus making it possible for it to be used for the preparation of yarns mixed with natural fibres, such as wool for example. The process for their production involves treatment of the material with enzymes of the nitrile hydratasis class obtained from *Brevibacterium imperiale*.

18 Claims, 2 Drawing Sheets

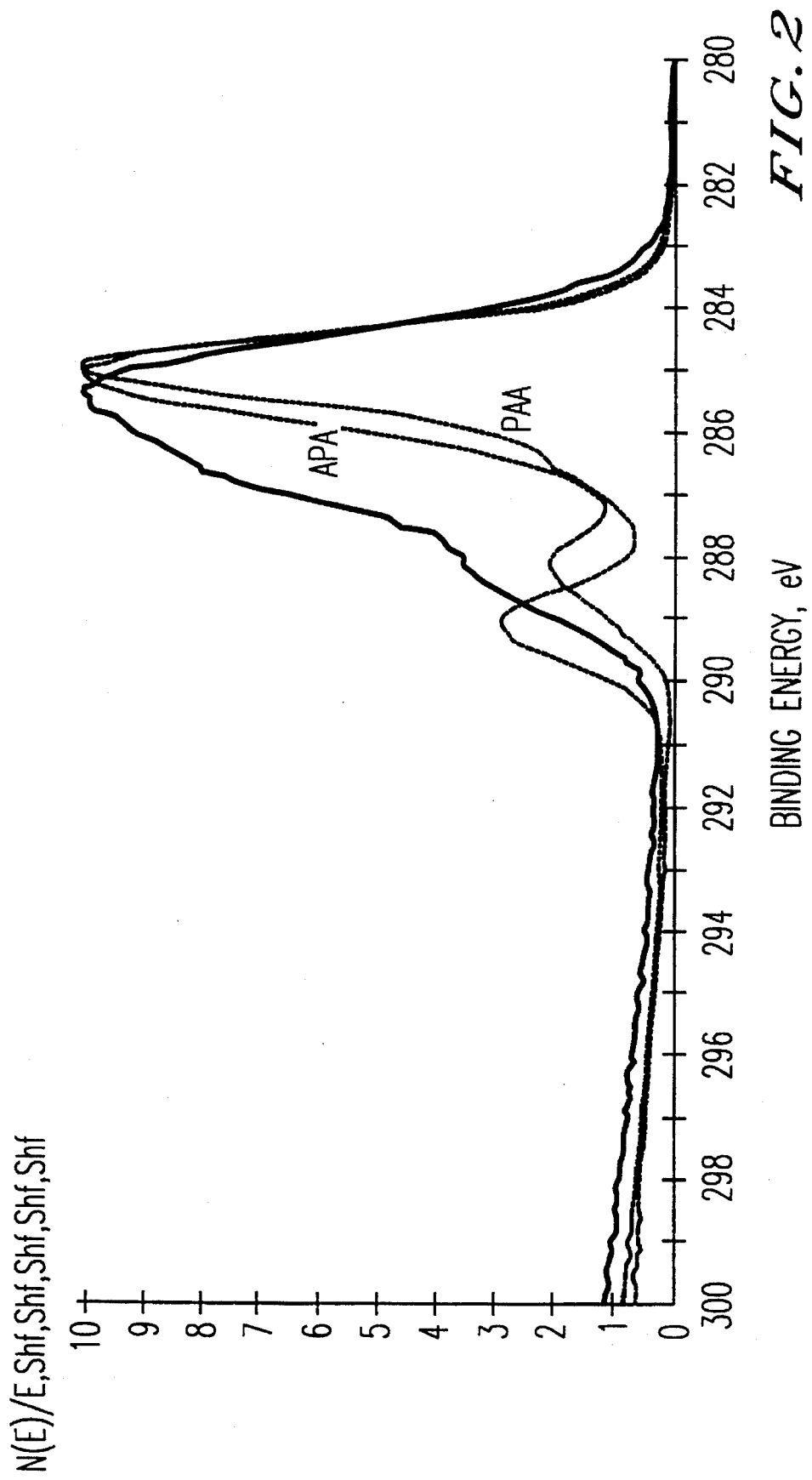

MODIFIED MATERIALS BASED ON POLYACRYLONITRILE AND PROCESS FOR THEIR PRODUCTION

This is a division of application Ser. No. 08/363,875 filed on Dec. 27, 1994, pending.

The present invention relates to modified materials based on polyacrylonitrile PAN (acrylic and modacrylic polymers or products obtained therefrom such as: fibres, woven, non-woven fabrics) and a process for their preparation.

An acrylic polymer means a linear polymer having at least 85% by weight of acrylonitrile in the chain.

More specifically the invention relates to acrylic and modacrylic polymers or products obtained therefrom modified on the surface by treatment with enzymes.

A modacrylic polymer is a linear polymer having at least 50% but not more than 85% by weight of acrylonitrile and quantities varying from 15% to 50% by weight of vinylidene chloride or bromide in the chain.

An acrylic or modacrylic fibre is a fibre obtained starting from an acrylic polymer or modacrylic polymer respectively by the dissolution of this in a suitable solvent and subsequent dry or wet spinning as is known in the art.

The materials thus treated have greater hydrophilic properties, which improve their comfort characteristics (in practice the fabrics are softer to handle). In addition, the possibility of dyeing them with acidic dyes makes them suitable for the preparation of yarns mixed with natural fibres such as wool.

Various examples of enzymatic processes for the preparation of polymers modified on the surface are mentioned in literature. These however refer only to natural polymers. (Borgondo, E. Fornelli. S., 1992, Nuova Selezione Tessile, May 1992, 116).

In the case of synthetic polymers, the known methods are mainly based on the action of strong chemical reagents or physical treatments. The purpose of these treatments is to introduce new functional chemical groups or to modify the groups already present on the surface of the fibres.

For example patents EP 397119 and EP 247975 describe the treatment of acrylic fibres with strongly reactive chemical reagents.

The treatment causes the conversion of the —CN groups into —COOH groups, thus increasing the surface hydrophilic property of the fibres.

Another example of chemical modification for improving the hydrophilic property of the materials based on polyacrylonitrile is the transformation of the —CN groups into —COOX groups, wherein X is a cation such as K or Na.

The reaction (saponification) can take place both under heterogeneous conditions, i.e. non-dissolved polymer (Geller, A. A., et al., 1974, J. Polym. Scien. 12,2327) or under homogeneous conditions (Sanli. O. 1990 Eur. Polym. J. 26,9).

In the first case, the reaction is influenced by the overmolecular architecture of the polymer and it is therefore not easily governable.

In the second case it is necessary to use organic solvents which are capable of dissolving the polymer.

In both cases, however, both the acid and the amide are often obtained and in addition drastic reaction conditions are required together with the presence of strong concentrations of bases (for example 25% KOH).

Generally, however, all the chemical processes used involve the use of organic solvents and dangerous reagents (alkalies and acids) which can also create safety problems, environmental problems and difficulties for treatment of the by-products.

In addition, these processes are difficult to repeat and control (they often lead to the undesired dissolution of the fibre).

The surface modification of synthetic polymers can also be obtained by drastic physico-chemical treatments or particular techniques at high energy density.

For example, the use of radiation (gamma or X rays) or gaseous phases in partially ionized states, such as plasma (GB 2.105,729, 1981), belong to this group of techniques. However the problems of safety and health, which the introduction of these techniques can create in an industrial process, are enormous especially if there are considerable quantities of materials to be treated.

In addition to these, there are also problems of a technical nature.

For example, when plasma is used there is:

the impossibility of controlling the relative quantity of —OH, —COOH or ester groups introduced;

lack of specificity with consequent heterogeneity of the modified surface;

the necessity of operating under vacuum (at least $1 \times 10^{-3}$ torr) and consequently considerable technical problems when large quantities of material are treated.

It would therefore be of great practical importance to overcome the problems arising from the use of both chemical and physico-chemical treatments of synthetic polymers.

The development of alternative technologies, such as those for example based on the use of a biological system, either eliminates or reduces the above disadvantages. These systems, in fact, generally have the following advantages:

it is possible to operate in an aqueous medium under moderate conditions of both temperature (not higher than 30° C.) and pH (approximately neutral);

specific modifications can be obtained: the use of particular enzymes or enzymatic products make it possible to convert the —CN groups to —CO—NH$_2$ without further hydrolysis of the amide to acid;

highly technological equipment such as that used for treatment with plasma is not required;

the degree of modification of the polymer, and consequently its final characteristics, can be controlled.

However, biological treatment capable of modifying the surface properties of synthetic polymers, including polyacrylonitrile has not been described so far and the application of these techniques is for the moment limited to the study of the biodegradation of synthetic polymers.

The Applicant has now succeeded in obtaining modified materials based on polyacrylonitrile with improved properties both with respect to the comfort and possible applications.

The Applicant has, in addition, succeeded in preparing a simple and easily applicable process for the preparation of the above material, based on the use of a biological system.

The present invention therefore relates to materials based on polyacrylonitrile (polymers or manufactured goods) modified by treatment with enzymes characterized in that amidic groups are present on their surface.

A second aspect of the present invention relates to the process for the preparation of polymers or manufactured goods modified on the surface, characterized in that the polymer or manufactured goods are treated with enzymes of the nitrile hydratasis class.

The manufactured goods obtained have a greater hydrophilic property, which improves the comfort characteristics of the weaves (they are softer to the touch) In addition, the possibility of dyeing them with acidic dyes enables the preparation of yarns mixed with natural fibres such as wool.

The process of the present invention comprises all the advantages mentioned above for the biological systems, consequently eliminating the drawbacks associated with chemical and physico-chemical systems.

Enzymes of the nitrile hydratasis group are present in various micro-organisms. *Brevibacterium imperiale*, for example, produces them in high quantities. Some of these micro-organisms, moreover, are already used industrially for the production of commodities. (Kobayashi, M., et al., 1992, Tibtech. 10,40–2). An example is represented by the production of acrylamide starting from acrylonitrile by the Japanese company Nitto.

The strain CBS 49874 of *Brevibacterium imperiale* available at the international centre Centraal bureau voor Schimmelcultures, Baarn, Delft, The Netherlands, was used for the embodiment of our process.

The strain belongs to a first group of isolated *Brevibacterium imperiale* strains shown about fifteen years ago for the production of acrylamide (Arnoud, A., et al., 1976, Acad. Sci. Paris, 287,5713).

The enzymes produced by *B. imperiale* are capable of hydrolizing the nitrile group to amide and then act on the surface —CN groups of the acrylic or modacrylic polymer according to the following reaction:

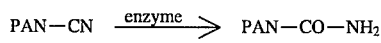

The polymer subjected to the reaction can be in the form of a non-spun polymer having a varying particle size, or in the form of a fibre, woven or non-woven fabric.

It can also be a pure homopolymer (100% acrylonitrile) or its synthesized copolymer starting from a mixture of up to 10% by weight of other monomers such as vinylesters (for example vinyl acetate) or acrylates, or its copolymer containing up to 50% by weight of vinylidene chloride.

The chemical modification by enzymes of the —CN groups which causes the formation of —CO—$NH_2$ groups is confirmed by surface analyses of the materials.

Techniques which reflect the properties of the material as a whole (such as IR, NMR) cannot be used because they are not sensitive enough to show the surface modification of the polymer, as the modified —CN groups are only a small part of the whole.

The most suitable technique is XPS (X-ray Photoelectron Spectroscopy) or ESCA (Electron Spectroscopy for Chemical Analysis) and the apparatus used is a Perkin Elmer PHI 5500 ESCA System (X-ray source at 14 KV, 200 W).

The analysis extends for a thickness of about 6 nonometers of material.

From an examination of the data provided in the examples, the conclusion can be reached that the enzymatic modification consists in the hydrolysis of the —CN groups to amide without any further hydrolysis of the amide to carboxylic acid.

The contact angle of the fibre modified by enzymatic treatment changes with respect to the non-treated fibre.

For example, the contact angle of the whole acrylic polymer (comonomer: 5% vinyl acetate) is 53° whereas the modified one is 30°±7°.

This variation indicates a significant increase in the hydrophilic degree of the surface of the polymer after the enzymatic treatment.

The following examples provide a better illustration of the present invention but do not limit its scope, which is described in the enclosed claims.

EXAMPLE 1

The enzymatic products were obtained according to the following process:

Fermentations of *B. imperiale* were prepared in 2-liter flasks containing 0.5 l of culture broth for a total volume of 3 l. A YMPG culture medium was used, consisting of yeast extract (3 g/l), malt extract (3 g/l), peptone (5 g/l). After sterilization of the medium, glucose was added under sterile conditions up to a final concentration of 10 g/l. The preinoculum was prepared in a YMPH medium, of which 50 ml were removed to inoculate each flask. After 72 hours of culture at 28° C., 200 rpm, the cells were centrifugated and resuspended in a 100 mM phosphate buffer, pH 7. On an average 15±3 g/l of fermentation broth of cells (humid weight) were obtained. The cells were then lysated by ultrasonic treatment at 250 watts for 60 secs, for 7 break cycles with intervals for cooling periods. The cellular lysis was spectrophotometrically controlled, by a measurement at 260 nm of the nucleic acids present in the surnatant liquid, after centrifugation of the lysis.

The test to quantitatively check the activity of the nitrile hydratasis enzyme is carried out under the following conditions: phosphate 100 mM, pH 7 (1 ml), sample (10–50 μl), acrylonitrile (5 μl), temperature 30° C. (Hjort, C. M., et al., 1990, Tech. Biotechnol., 48,217).

The formation of the hydrolysis product, acrylamide, was followed spectrophotometrically at 235 nm as a function of time.

The concentration of the hydrolysis product was calculated using an extinction coefficient of $1106\ cm^{-1}M^{-1}$.

The unit of enzymatic activity is defined as the quantity of enzyme capable of transforming 1 μmole of substrate per minute at 30° C.

On an average $6\pm2\times10^5$ U were obtained per liter of lysated cells.

EXAMPLE 2

For the treatment of the polymer enzymatic products were used consisting of whole or partially purified cellular lysates obtained from standard *B. imperiale* cultures (YMPH medium, pH 7, 28° C.).

The cells were lysated by ultrasonic treatment and the lysate, consisting of a turbid suspension of drift and cellular organelles, was used as such or centrifuged. In the latter case, the precipitated product was disposed of. The centrifugation causes a partial loss of the enzymatic activity.

For the enzymatic modification tests the polymer with a different particle size was used, for example with an average particle diameter of between 10 and 200 μm. To facilitate the interaction between the enzyme (soluble in a buffer solution) and polymer (insoluble in water) in some cases 2% v/v of dimethylformamide (DMF) or dimethylacetamide (DMAC) was added. DMF and DMAC are solvents which are capable of dissolving the polymer. To ensure that the presence of proteins or nucleic acids possibly non-specifically absorbed by the polymer cannot interfere with the analysis of the surface modification of the polymer, the reference polymer was treated in the same way as the samples, i.e. it was put in contact, for the same reaction time, with the cellular lysate or surnatant, after deactivating however the enzymatic activity present by treatment at 35° C. for 24 hours.

The granular polymer was left to decant and the surnatant liquid eliminated.

Similarly three washing cycles with water were repeated, centrifuging each time at 3–4000 rpm for 2–3 minutes and the surnatant liquid was disposed of. The polymer was then filtered on Gooch washed with 50% ethanol (3 times), water (3 times) and finally acetone (3 times).

The test samples were then dried under vacuum (with a water pump). The fibre and weave were treated in the same way, without centrifugation.

The following test samples were then treated as described in detail in examples 3-7.

1. acrylic polymer treated with whole cellular lysate
3. acrylic polymer treated with whole cellular lysate +2% DMF.
2. acrylic polymer treated with surnatant liquid of the centrifuged lysate.
4. acrylic polymer treated with surnatant liquid of the centrifuged lysate +2% DMF
7. acrylic polymer as such (treated with whole deactivated cellular lysate)
8. acrylic polymer as such (treated with inactivated surnatant of the centrifuged lysate)

After 24 hours the samples were washed and analyzed to show that the enzymatic attack had taken place.

At the same time samples of spun polymer (fiber) and woven were also prepared. The average diameter of the fibers can be between 2–30 μm.

5. acrylic fiber treated with whole lysate
6. acrylic fiber treated with whole lysate +2% DMF
9. acrylic fiber treated with whole deactivated lysate
10. fabric as such
11. fabric treated with whole cellular lysate To show the surface modification of the polymer, of the fiber and of the fabric, the XPS (X-ray Photoelectron Spectroscopy) or ESCA (Electron Spectroscopy for Chemical Analysis) technique was used.

The analysis is extended for a thickness of about nanometers of the material.

The results of the XPS analysis on the polymer, fiber and woven samples prepared as described, are shown in Table 1.

The results refer to the relative percentages of Oxygen, Nitrogen and Carbon present on the surface of the samples.

TABLE 1

| No. | conditions | % O | % C | % N |
|---|---|---|---|---|
| | granular polymer | | | |
| 7 | as such | 4.8 | 77.5 | 17.7 |
| 1 | whole lysate | 12.8 | 74.6 | 12.6 |
| 3 | whole lysate + 2% DMF | 12.7 | 71.7 | 15.6 |
| 8 | as such | 4.8 | 78.5 | 16.6 |
| 2 | centrifuged lysate | 12.8 | 72.9 | 14.3 |
| 4 | centrifuged lysate + 2% DMF | 12.0 | 73.3 | 14.7 |
| | fibre | | | |
| 9 | as such | 9.0 | 77.0 | 14.0 |
| 5 | whole lysate | 12.5 | 76.5 | 11.0 |
| 6 | whole lysate + 2% DMF | 13.8 | 74.1 | 12.1 |
| | woven fabric | | | |
| 10 | as such | 8.5 | 77.3 | 14.2 |
| 11 | whole lysate | 10.0 | 76.5 | 13.5 |

As can be seen, the content of surface oxygen present in the polymer, fiber and woven significantly increases, as can be expected when —CN groups are transformed into amidic groups.

At the same time, the relative percentage of —CN decreases. The O/C ratio increases indicating a significant hydrophilization of the surface.

It should also be noted that the same effects are obtained both with the whole cellular lysate, richer in proteins and nitrile hydratasic enzymatic activity (12.000 Units/ml), and with the surnatant of the centrifuged lysate, poorer in nitrile hydratasic enzymatic activity (about 650 Units/ml).

Figure 1B:
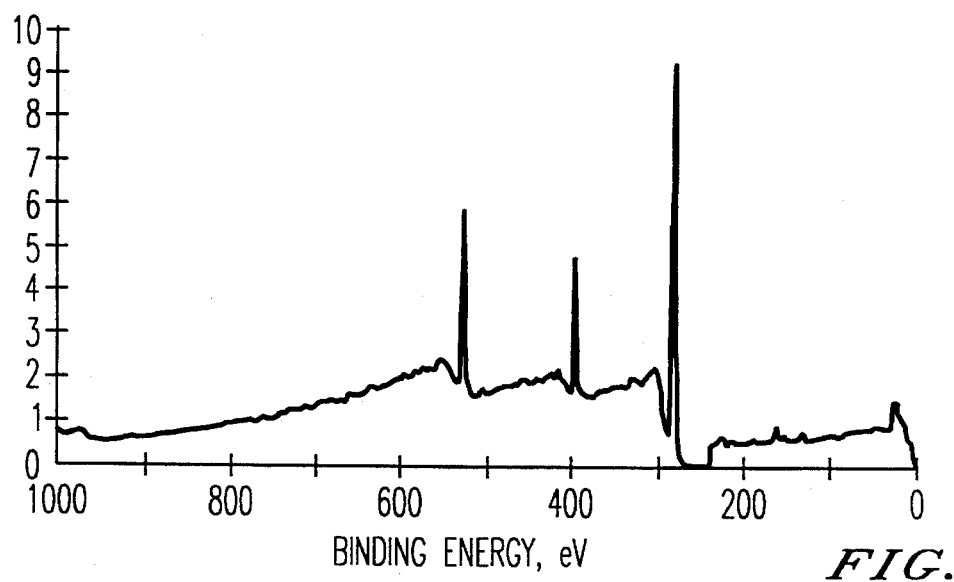

FIG. 1 shows the XPS spectrum of the polymer as such (A) and treated polymer (B) (sample 1). The peak around 530 eV refers to the oxygen, whereas those around 395 and 290 are of the nitrogen and carbon, respectively.

Integration of the peaks gives the relative percentages of the atoms present on the surface.

FIG. 2 shows the XPS peak of carbon of the granular acrylic polymer (continuous line) which covers those obtained from the analysis of the polyacrylic acid (APA) and polyacrylamide (PAA dotted line).

As can be seen, in the treated polymer there is a high energy bond band, around 285 eV, typical of the amidic group. In fact this band is characteristic of the PAA spectrum.

There is no component on the other hand with higher energies typical of the carboxylic group of APA. It can be concluded that the enzymatic modification consists in the hydrolysis of the —CN groups to amide without further hydrolysis of the amide to carboxylic acid.

EXAMPLE 3

1 g of granular acrylic polymer (average particle size 30 μm) was put in contact (in a 100 ml flask) with 50 ml of *B. imperiale* cellular lysate in a 100 mM phosphate buffer, pH 7, (or surnatant after centrifugation) having an activity of about 8.000–12.000 U/ml (or in the case of the surnatant 400–700 U/ml). The suspension was vigorously stirred at 200–250 rpm. The temperature was maintained at 20°±1° C. After 24 hours the polymer was decanted and washed, after disposing of the surnatant. The results of the XPS analysis are shown in Table 1 sample 1, and sample 2 in the case of reaction with surnatant.

EXAMPLE 4

1 g of granular acrylic polymer (average particle size 45 μm) was reacted (in a 100 ml flask) with 50 ml of *B. imperiale* cellular lysate in a 100 mM phosphate buffer, pH 7, (or surnatant after centrifugation) having an activity of about 8.000–12.000 U/ml (or in the case of the surnatant 400–700 U/ml). The suspension was vigorously stirred at 200–250 rpm for 24 hours. The temperature was maintained at 20°±1° C. The results of the XPS analysis are very similar to those shown in Example 3.

EXAMPLE 5

1 g of granular acrylic polymer (average particle size 30 μm) was reacted (in a 100 ml flask) with 50 ml of *B. imperiale* cellular lysate in a 100 mM phosphate buffer, pH 7, (or surnatant after centrifugation) having an activity of about 8,000–12.000 U/ml (or in the case of the surnatant 400–700 U/ml). 1 ml of dimethylformamide or dimethylacetamide (2% v/v) was added to the mixture. The suspension was vigorously stirred at 200–250 rpm. The temperature was maintained at 20°±1° C. The results of the XPS analysis are shown in Table 1 sample 3, and sample 4 (in the case of reaction with the surnatant).

EXAMPLE 6

500 mg of acrylic fiber (average diameter of the microfibers 5 μm) were put in contact (in a 500 ml flask) with 30 ml of *B. imperiale* cellular lysate in a 100 mM phosphate buffer, pH 7, (or surnatant after centrifugation) having an activity of about 8,000–12,000 U/ml (or in the case of the surnatant 400–700 U/ml). The mixture was vigorously stirred at 200–250 rpm. The temperature was maintained at 20°±1° C. After 24 hours the fiber was washed as described above. The results of the XPS analysis are shown in Table 1 sample 5, and sample 6 (in the case of reaction with surnatant).

EXAMPLE 7

A piece of plain knitted Jersey having a weight of 20 g/m² (20×20 cm) was put in contact (in a 500 ml flask) with 50 ml of *B. imperiale* cellular lysate in a 100 mM phosphate buffer, pH 7 having an activity of about 8,000–12,000 U/ml After 24 hours of vigorous stirring (200–250) at 20°±1° C., the piece of weave was washed. The results of the XPS analysis are shown in Table 1, sample 11.

EXAMPLE 8

1 gram of granular acrylic polymer (average particle size 45 μm) treated with cellular lysate from *Brevibacterium imperiale* (as described in example 2) and 1 gram of standard acrylic polymer (not enzymatically treated) were put in 2 hermetic flask each containing 50 ml of a solution (100 mg/l) of Polar Red B-01 Ciba, acidified with sulphuric acid at pH 2.1. The two samples were put in an oven for 60 min. at 98° C. After recovering the surnatant liquid, the samples were filtered on gooch and washed four times with water.

The standard polymer maintained the same starting colour (white), whereas the enzymatically treated polymer had become dark red.

The conditions used for the dyeing (pH, temperature and duration of treatment) are similar to those normally used for the dyeing of wool.

We claim:

1. A process for preparing modified polyacrylonitrile, comprising treatment polyacrylonitrile with an effective amount of a nitrile hydratasis enzyme at an enzymatically active temperature and pH, wherein surface —CN groups of said polyacrylonitrile are hydrolyzed to —CO—NH₂ groups, wherein said treating is carried out with stirring in the presence of 2,000–12,000 U/ml of said enzyme on 0.2–2 grams of said polyacrylonitrile, in a medium containing 100 mM phosphate buffer at pH 7, at a temperature of 10°–30° C. for 12–24 hours.

2. The process of claim 1, wherein said polyacrylonitrile is treated with whole or partially purified cellular lysates of Brevibacterium bacteria containing said enzyme.

3. The process of claim 2, wherein said Brevibacterium bacteria is *Brevibacterium imperiale*.

4. The process of claim 2, wherein said Brevibacterium bacteria is *Brevibacterium imperiale* CBS 49874.

5. The process of claim 1, wherein said medium further comprises 1–3% v/v of dimethyl formaldehyde.

6. A process for preparing modified polyacrylonitrile, comprising treating polyacrylonitrile with an effective amount of a nitrile hydratasis enzyme at an enzymatically active temperature and pH, wherein surface —CN groups of said polyacrylonitrile are hydrolyzed to —CO—NH₂ groups, wherein said polyacrylonitrile is in the form of a non-yarn polymer having an average polymer diameter between 10–200 microns.

7. A process for preparing modified polyacrylonitrile, comprising treating polyacrylonitrile with an effective amount of a nitrile hydratasis enzyme at an enzymatically active temperature and pH, wherein surface —CN groups of said polyacrylonitrile are hydrolyzed to —CO—NH₂ groups, wherein said polyacrylonitrile is in the form of a polymer yarn, fiber or weave, having an average fiber diameter between 10–30 microns.

8. The process of claim 1, wherein said polyacrylonitrile is an acrylonitrile homopolymer or copolymer of acrylonitrile and a vinyl ester or acrylate.

9. The process of claim 6, wherein said polyacrylonitrile is treated with whole or partially purified cellular lysates of Brevibacterium bacteria containing said enzyme.

10. The process of claim 9, wherein said Brevibacterium bacteria is *Brevibacterium imperiale*.

11. The process of claim 9, wherein said Brevibacterium bacteria is *Brevibacterium imperiale* CBS 49874.

12. The process of claim 6, wherein said medium further comprises 1–3% v/v of dimethyl formaldehyde.

13. The process of claim 6, wherein said polyacrylonitrile is an acrylonitrile homopolymer or copolymer of acrylonitrile and a vinyl ester or acrylate.

14. The process of claim 7, wherein said polyacrylonitrile is treated with whole or partially purified cellular lysates of Brevibacterium bacteria containing said enzyme.

15. The process of claim 14, wherein said Brevibacterium bacteria is *Brevibacterium imperiale*.

16. The process of claim 14, wherein said Brevibacterium bacteria is *Brevibacterium imperiale* CBS 49874.

17. The process of claim 14, wherein said medium further comprises 1–3% v/v of dimethyl formaldehyde.

18. The process of claim 14, wherein said polyacrylonitrile is an acrylonitrile homopolymer or copolymer of acrylonitrile and a vinyl ester or acrylate.

* * * * *